United States Patent
Ikeda et al.

[11] Patent Number: 6,022,581
[45] Date of Patent: Feb. 8, 2000

[54] AGGREGATE CRYSTALS OF PHOSPHORIC ACID/LYSINE/MAGNESIUM COMPOSITE SALT AND PROCESS FOR PRODUCING THE SAME

[75] Inventors: Toru Ikeda; Toyoto Hijiya; Kenichi Mori; Toshihide Yukawa; Tadashi Takemoto, all of Kawasaki, Japan

[73] Assignee: Ajinomoto Co., Inc., Tokyo, Japan

[21] Appl. No.: 08/919,500

[22] Filed: Aug. 28, 1997

[30] Foreign Application Priority Data

Aug. 28, 1996 [JP] Japan .................................... 8-226532

[51] Int. Cl.$^7$ ...................................................... A23J 1/00
[52] U.S. Cl. ................................ 426/656; 426/2; 426/74; 426/630; 424/438
[58] Field of Search ................................ 426/2, 74, 656, 426/630; 424/438

[56] References Cited

U.S. PATENT DOCUMENTS 5,744,178   4/1998   Ikeda et al. .

FOREIGN PATENT DOCUMENTS 0744396   11/1996   European Pat. Off. .
WO96/17822   6/1996   WIPO .

*Primary Examiner*—Anthony J. Weier
*Attorney, Agent, or Firm*—Oblon, Spivak, McClelland, Maier & Neustadt, P.C.

[57] ABSTRACT

Spherical aggregate crystals of a phosphoric acid/lysine/magnesium composite salt represented by formula (1):

$$R_a Mg_b H_c PO_4 \cdot (H_2O)_n \tag{1}$$

where

R is a lysine cation;
a is 0.15 to 1.0;
b is 1.0 to 1.42;
c is 0 to 0.3;
n is 0 to 10; and
$a+(2\times b)+c=3$.

20 Claims, 7 Drawing Sheets

AGGREGATE CRYSTALS OF PHOSPHORIC ACID/LYSINE/MAGNESIUM COMPOSITE SALT AND PROCESS FOR PRODUCING THE SAME

BACKGROUND OF THE INVENTION

1. Field of the Invention

The present invention relates to an animal feed additive composition. More specifically, the present invention relates to a powdery or granulate ruminant feed additive composition which is stable in a rumen of a ruminant and releases lysine in the abomasum and lower digestive organs thereof, as well as to a powdery or uniformly granulate aquacultural animal feed additive composition which is stable in fresh water or seawater and releases lysine in digestive organs of aquacultural animals.

2. Description of the Background

When biologically active substances such as amino acids, vitamins and the like are orally administered directly to ruminants such as cow, sheep and the like, most of these substances are decomposed by microorganisms in the rumen, and are, therefore, not utilized effectively. Accordingly, rumen by-pass preparations for use in ruminants in which these biologically active substances are protected from decomposition by microorganisms in the rumen but are digested and absorbed in the abomasum and lower digestive organs are important in the field of ruminant feed, nutrients and chemicals.

When biologically active substances such as amino acids, vitamins and the like are added to the formula feed used in the cultivation of aqua-animals and the mixture is administered to cultivated aqua-animals, most of the biologically active substances are eluted into the water and diluted therein owing to the water-solubility thereof, and these are, therefore, not utilized effectively. Accordingly, a feed additive composition for feeding aquacultural animals which protects these biologically active substances from the elution into water but allows digestion and absorption in the digestive organs of aquacultural animals is important in the field of feed, nutrients, chemicals and the like for aquacultural animals.

With respect to ruminant feed additives containing a biologically active substance, methods are known in which a biologically active substance is dispersed in a matrix formed of a hydrophobic substance such as fats and oils or a protective substance, such as a basic high-molecular substance, and the dispersion is granulated, or where a core containing a biologically active substance is coated with a hydrophobic substance such as fats and oils or an acid-sensitive substance, such as a basic high-molecular substance.

However, in the method where the biologically active substance is dispersed into the protective substance, the biologically active substance is present near the surfaces of the particles. Accordingly, when the active substance must be well-protected, the content of the biologically active substance must be significantly decreased. Since the residence time of the water-soluble biologically active substance in the rumen is between 10-odd hours and several days, the biologically active substance cannot be protected sufficiently.

Further, a method where the biologically active substance-containing core is coated with the acid-sensitive high-molecular substance or the hydrophobic protective substance has been also proposed. However, in view of production techniques which have been used in recent years, mechanical granulation and/or coating destruction occurs due to mixing or pulverization with another feed composition. As a result, the stability in the rumen is impaired in many cases. Therefore, this composition is not desirable as a multi-purpose feed additive composition.

Thus, it is advisable that a feed additive which can withstand mixing or pulverization with another feed composition be in the form of a powder or uniform granules and prevent release of a biologically active substance in the rumen and allow elution of the biologically active substance in the abomasum and lower digestive organs.

On the other hand, with respect to feed additives for aquacultural animals which contain a biologically active substance, a method in which a core containing a biologically active substance is coated with hydrophobic substances such as fats and oils has been proposed. Regarding a method in which a biologically active substance is coated with a hydrophobic protective substance, for example, Japanese Laid-Open (Kokai) No. 173,060/1992 proposes an aquacultural animal feed starting material in which a water-soluble amino acid and/or water-soluble amino acid derivatives are coated with animal fats or waxes which are solid at room temperature, as well as a process for producing the same.

However, the method of coating a core containing a biologically active substance with a hydrophobic protective material causes, in view of the production techniques used in recent years, mechanical destruction of granules and/or coating due to mixing or pulverization with other formula feed starting materials, thereby impairing the protection in water in many cases. Thus, this composition is not useful as a multipurpose feed additive composition. In addition, the administration of coated particles alone is problematic in that it is not appropriate for cultivated aqua-animals and the necessary amount of the feed cannot be consumed.

Thus, it is advisable that a feed additive which can withstand mixing or pulverization with another aquacultural animal feed composition be in the form of a powder or uniform granules and prevent release of a biologically active substance in water and allow elution of the biologically active substance in the digestive organs of aquacultural animals. However, when lysine is used to improve nutrition of the feed, the only known lysine-containing composition which takes the form of a powder or uniform granules and which is insoluble in neutral water and is soluble in the acid of digestive organs is phosphorus wolframate.

As a substance having such desirable properties, the present inventors have found a phosphoric acid/lysine/magnesium composite salt (hereinafter referred to as the "composite salt") represented by the following formula (1), which is composed of lysine, magnesium, phosphoric acid (or phosphate) and, optionally, water.

$$R_a Mg_b H_c PO_4 \cdot (H_2O)_n \tag{1}$$

where

R represents a lysine cation, a is between 0.15 and 1.0, b is between 1.0 and 1.42, c is between 0 and 0.3, a+(2×b)+c=3, and n is between 0 and 10.

Four processes are known for producing this salt. These processes are described in EP 0 744 396 A1, incorporated herein by reference in its entirety.

In the first process, a secondary phosphate of magnesium is dispersed into a large amount of a basic aqueous solution of lysine, and the dispersion is heated.

In the second process, a magnesium neutral salt and phosphoric acid are mixed at a molar ratio of 1.0 to 1.45:1.0 in a large amount of a basic aqueous solution of lysine.

In the third process, a primary phosphate solution of lysine is mixed with from 1.0 to 1.45 mols of magnesium hydroxide or magnesium oxide.

In the fourth process, a solution obtained by mixing and neutralizing a basic aqueous solution of lysine with phosphoric acid at a molar ratio of 0.05 to 0.9:1.0 is mixed with from 1.0 to 1.45 mols of magnesium hydroxide or magnesium oxide.

The desired composite salt can be isolated and purifed by subjecting the magnesium salt obtained by these process to appropriate solid-liquid separation to remove excess lysine through washing. However, when the salt is actually made by one of these processes, the reaction solution solidifies or gels, or microfine crystals form, making the stirring and/or the solid-liquid separation extremely difficult.

In order to isolate the desired composite salt from such a reaction mixture which is solidified or gelled, a method is employed in which the stirring can be conducted upon diluting the product with a large amount of water or the solid-liquid separation can be conducted by milling the solid mass in a large amount of water. The production can be conducted on a small scale by this method. However, the use of a special equipment is required for production on an industrial scale, which is undesirable.

Further, when microfine crystals are formed, the solid-liquid separation takes considerable time. Therefore, in production on an industrially large scale, a large-sized separator or a large number of separators are required, increasing the cost for the separation equipment. Accordingly, this method is uneconomical. Further, in the solid-liquid separation from the reaction solution having poor slurry properties, the crystals separated tend to contain a mother liquor, which reduces the purity of the crystals.

The above-mentioned four processes for producing the composite salt are suitable for the production on a small scale, but require much improvement for production on an industrial scale.

SUMMARY OF THE INVENTION

An object of the present invention is to provide a process for producing the composite which may be easily conducted on an industrial scale.

The present inventors have assiduously conducted investigations to achieve the above-mentioned object, and have found that a reaction solution which does not solidify may be obtained by simultaneously adding lysine, a magnesium component and a phosphoric acid component to a slurry containing the composite salt, while retaining the slurry alkaline, followed by mixing the components. Further, it has been found that when the addition is conducted such that the temperature of the slurry containing the composite salt is maintained at 50° C.or higher and the pH is kept constant, the fluidity of the slurry is improved and the solid-liquid separation procedure used to isolate the composite salt may be easily conducted. In addition, the composite salt obtained by this process is in the form of spherical aggregate crystals having a relatively uniform diameter, unlike the aggregate crystals having an uneven form and an uneven size which are produced by the above-mentioned four processes. This uniform shape is believed to contribute toward improving the slurry properties. These findings have led to the completion of the present invention.

That is, the present invention relates to a spherical aggregate crystal of a composite salt represented by formula (1):

$$R_a Mg_b H_c PO_4 \cdot (H_2O)_n \tag{1}$$

where

R represents a lysine cation, a is between 0.15 and 1.0, b is between 1.0 and 1.42, c is between 0 and 0.3, a+(2×b)+c=3, and n is between 0 and 10.

The objects of the present invention may also be achieved with compositions containing this salt as well as processes of making the composite salt which produce spherical aggregate crystals.

A more complete appreciation of the invention and many of the attendant advantages thereof will be readily obtained as the same becomes better understood by reference to the following detailed description when considered in connection with the accompanying drawings.

DETAILED DESCRIPTION OF THE INVENTION

An important feature of the present invention is that the composite salt is in the form of aggregate spherical crystals, in contrast to the crystals obtained by any of the four processes described above. The term "aggregate spherical crystal" refers to an assembly of smaller, component crystals which are in direct contact with each other to form a larger crystal that has a spherical shape (see FIG. 1). These spherical aggregate crystals are extremely important because the slurries used to make them are much easier to stir and separate easily into the solid and liquid components. Both of these effects contribute to reducing the production costs for preparing the composite salt, making production of the crystal on an industrial scale much more economical.

The composite salt of the present invention is roughly grouped into (1) aggregate crystals comprised of either a first or a second crystal component, discussed below, (2) aggregate crystals comprised of a mixture of the first and second crystal components and (3) aggregate crystals formed of a mixture of magnesium tertiary phosphate ($Mg_3(PO_4)_2$) and/or magnesium secondary phosphate ($MgHPO_4$) crystals and the above-mentioned first and/or second crystal components.

The first type of crystal component is a phosphoric acid/lysine/magnesium composite salt in which, in formula (1), a is 1, b is 1, c is 0, a+(2×b)+c=3, and n is 2. This is a crystal component in which in the powder X-ray diffraction spectrum using copper K$\alpha$ rays, main peaks are observed at angles (θ) of approximately 3.7°, approximately 7.4°, approximately 18.5°, approximately 18.8°, approximately 20.7°, approximately 22.2°, approximately 29.7° and approximately 32.3°.

The second type of crystal component is a phosphoric acid/lysine/magnesium composite salt in which, in formula (1), a is 0.21 to 0.25, b is 1.325 to 1.395, c is 0 to 0.1, a+(2×b)+c=3, and n is 0 to 5. This second type of crystal component is one in which in the powder X-ray diffraction spectrum using copper K$\alpha$ rays, main peaks are observed at angles (θ) of from approximately 6.0° to approximately 6.5°, from approximately 7.4° to approximately 7.7°, approximately 15.6°, approximately 28.2° and approximately 32.5°.

In accordance with the present invention, these two types of crystal components may be obtained in the form of aggregate crystals composed of only one of the crystal components and also of aggregate crystals containing a mixture of the two types of crystal components. It is also possible to obtain aggregate crystals of a mixture of magnesium tertiary phosphate and/or magnesium secondary phosphate, either of which do not contain a lysine component, and either one or both of the two crystal components described above.

Figure 6A:
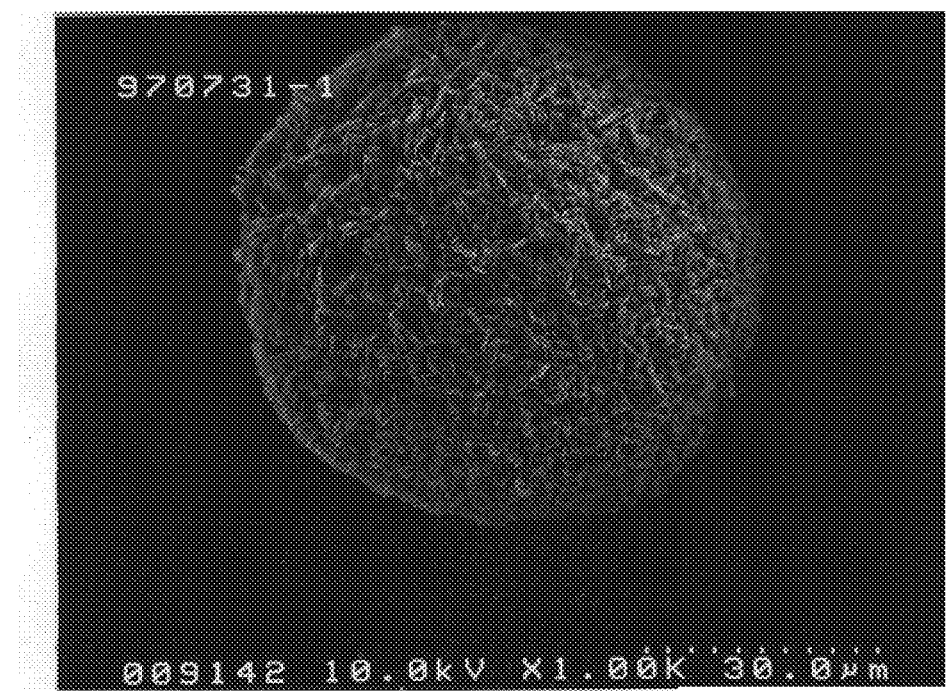
FIGS. 6a and 6b are optical electron photomicrographs of the spherical aggregate crystals obtained in Example 5 of the present disclosure. (A) first view (×1000), (B) second view (×1000).
Figure 6B:
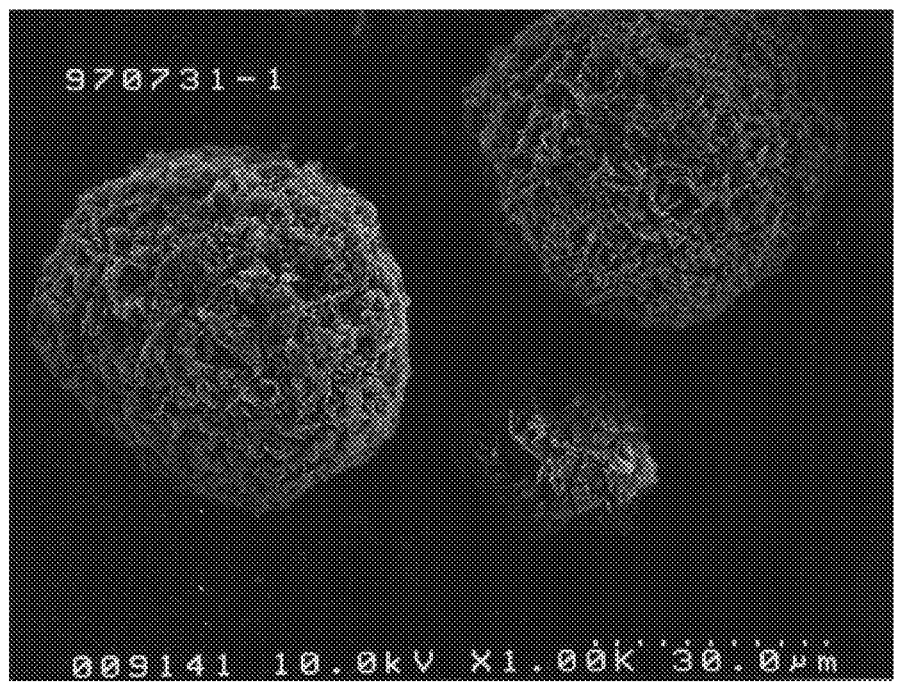
Figure 8A:
FIGS. 8a and 8b are optical electron photomicrographs of the spherical aggregate crystals obtained in Example 2 of the present disclosure. (A) first view (×1000), (B) second view (×1000).
Figure 8B:
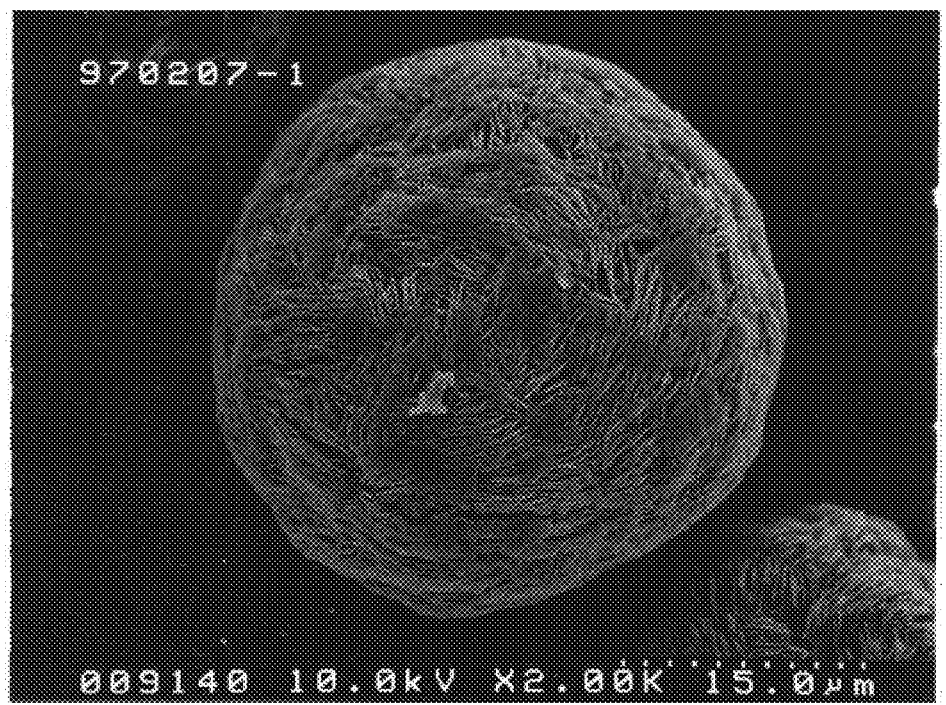

When the spherical aggregate crystals of the present invention are observed using an electron microscope, it is found that the component crystals are laminated crystals or plate crystals (e.g., see FIGS. 6 and 8). These crystals are radially aggregated or cylindrically aggregated, and spherically shaped by mechanical polishing through stirring. As used herein, the term "spherical" does not necessarily mean "completely round", but refers to a shape having a long axis/short axis ratio of from 1 to 2. This ratio range includes all specific values and subranges therebetween, including 1.1, 1.2, 1.3, 1.4, 1.5, 1.6, 1.7, 1.8 and 1.9. A schematic view of the aggregate crystal of the present invention is shown in FIG. 1.

The diameter of the aggregate crystal may vary depending on the production conditions. The crystal diameter usually between 5 and 100 $\mu$m. A mixture of aggregate crystals where each crystal has the same diameter may be easily obtained according to the present invention. In another embodiment, the aggregate crystals have substantially the same diameter. As used herein, "substantially the same diameter" means that at least 80% of the crystals have the same diameter, preferably at least 85%, more preferably at least 90% and, most preferably, at least 95% of the crystals have the same diameter. On the other hand, the crystals obtained by the above-mentioned four processes discussed above have an uneven shape, and there is a great difference in the diameter, from less than 1 $\mu$m to more than 300 $\mu$m in the same slurry.

The spherical aggregate crystals of the present invention, as compared with the conventional aggregate crystals having an uneven shape, make stirring of the reaction solution easy, are excellent with respect to solid-liquid separability of the reaction solution and have a high cleaning efficiency. Accordingly, the production equipment involves a low cost, the production procedure is easy, and the crystal purity of the isolated composite salt is high.

In formula (1), R represents a lysine cation, i.e., positively charged lysine. The lysine may have a formal charge of +1 or +2. This means that, formally, each of the amino groups are protonated and the carboxyl group is deprotonated, or one amino group is protonated and the carboxyl group is in the acid form. Alternatively, both amino groups are protonated and the carboxyl group is in the acid form. The lysine is preferably L-lysine. The variable n represents the water of hydration in the salt, and may be any number between 0 and 10. All of the ranges for a, b, c and n disclosed herein include the endpoints and all specific values and subranges therebetween.

Figure 5A:
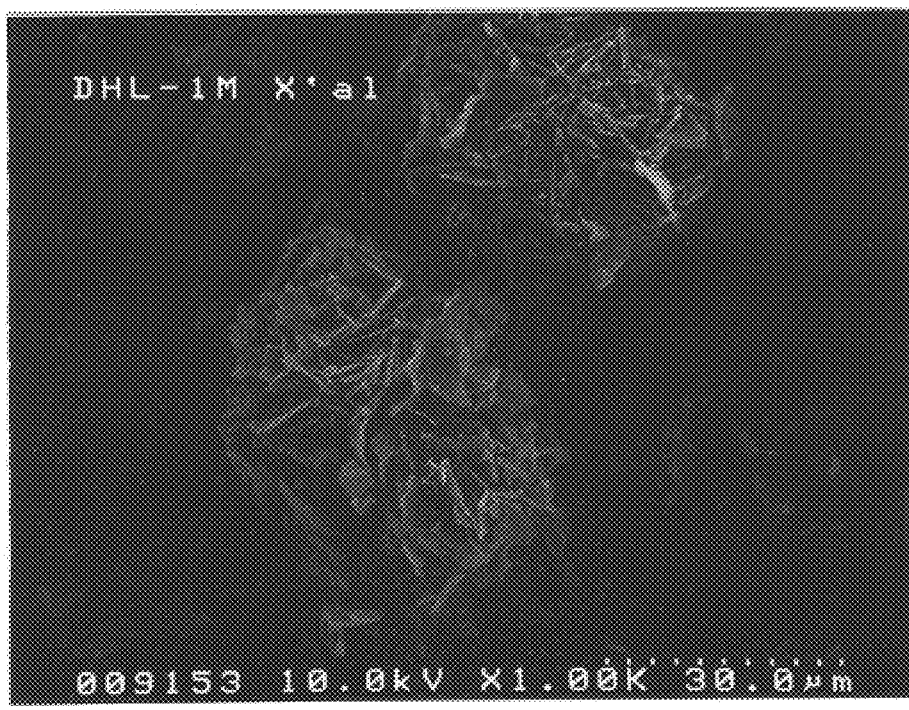
FIGS. 5a and 5b are optical electron photomicrographs of seed crystals obtained by the first method disclosed in EP 0 744 396.A1; (A) ×1000, (B) ×2000.
Figure 5B:
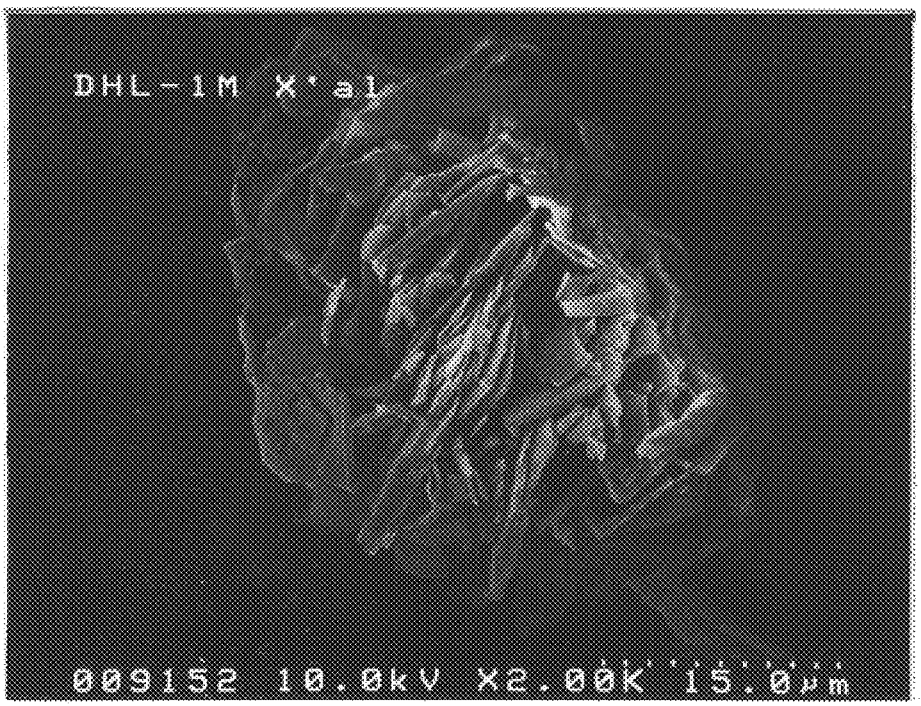
Figure 7A:
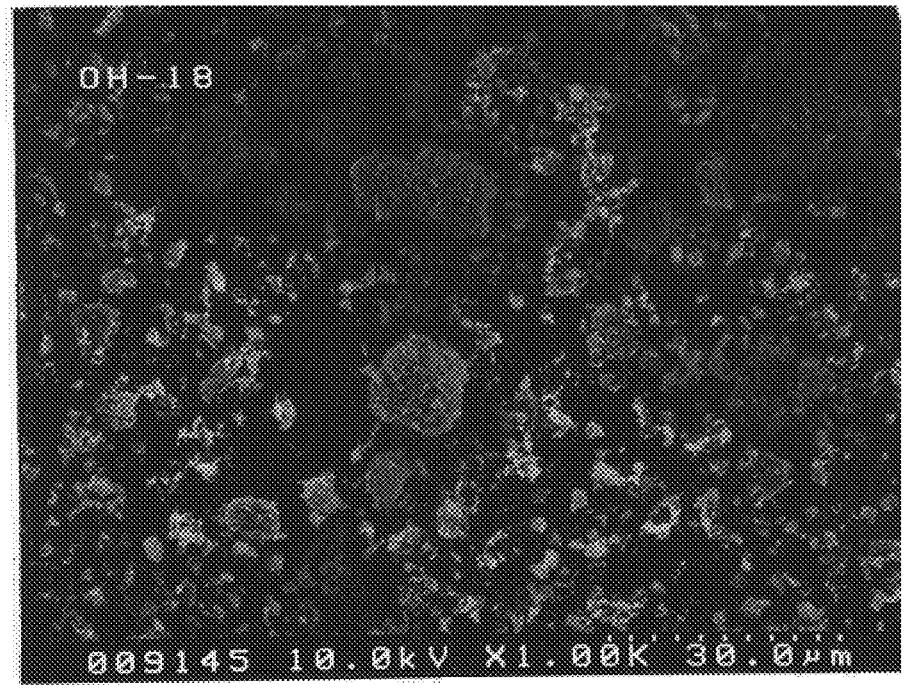
FIGS. 7a and 7b are optical electron photomicrographs of seed crystals obtained by the fourth method disclosed in EP 0 744 396.A1; (A) ×1000, (B) ×3000.
Figure 7B:
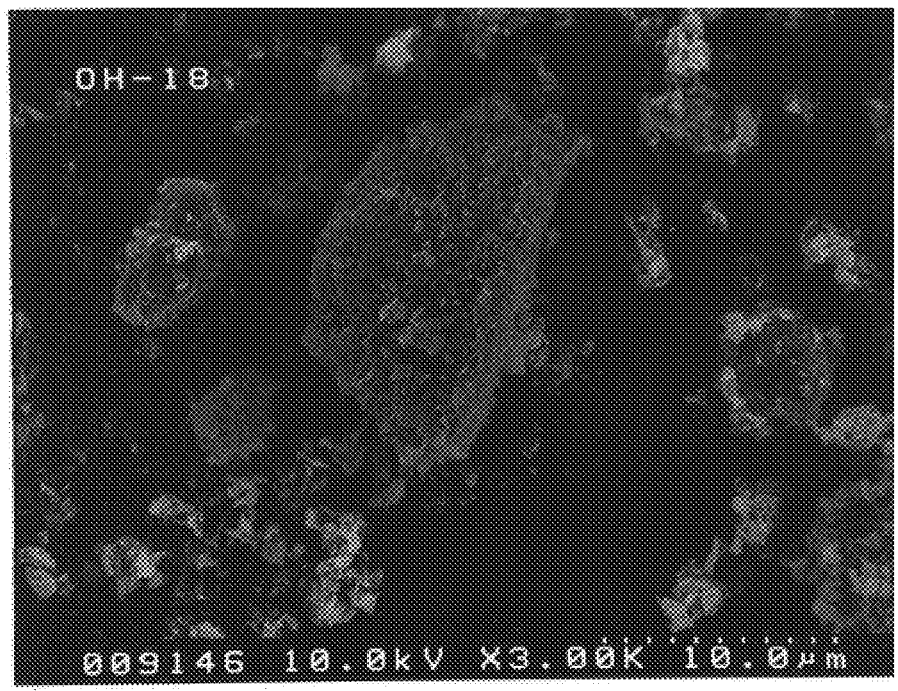

The spherical aggregate crystals of the composite salt of formula (1) may be produced by combining (1) lysine, (2) a magnesium component and (3) a phosphoric acid component with a slurry containing crystals of the composite salt of formula (1). Without being limited to any theory, the crystals already present in the slurry prior to the addition of (1)–(3) may act as seed crystals for the formation of the desired spherical aggregate crystals (see the Examples). The slurry containing the seed crystals may be prepared, for example, by any of the four processes described above (e.g., see FIGS. 5 and 7). The fourth process described above is particularly preferred. Alternatively, the seed crystals may be the spherical aggregate crystals of the present invention. The slurry is preferably aqueous. Components (1)–(3) are preferably added simultaneously to the slurry. The reaction is preferably conducted at alkaline pH and at a temperature of 50° C. or higher.

Examples of the phosphoric acid component include orthophosphoric acid ($H_3PO_4$) and salts thereof (e.g., metal salts, where the metals are alkali (e.g., sodium and potassium) or alkaline metals (e.g., calcium and magnesium). Examples of the magnesium component include magnesium-containing salts, such as magnesium hydroxide, magnesium oxide, magnesium chloride, magnesium sulfate and magnesium phosphate. However, when using starting materials other than orthophosphoric acid, magnesium hydroxide, magnesium oxide and magnesium phosphate, it is necessary to pay attention to the fact that salts such as sodium chloride, potassium sulfate and the like may be formed as by-products. The addition of other types of acid, such as, for example, hydrochloric acid, is not preferable because of dilution of the orthophosphoric acid. Accordingly, it is advisable to use a combination of orthophosphoric acid and magnesium hydroxide or magnesium oxide or a combination of acidic magnesium phosphate, orthophosphoric acid and/or magnesium hydroxide or magnesium oxide. The lysine used to make the composite salt may be the free amino acid, a hydrate thereof or an acid salt thereof.

In the reaction of forming the composite salt in the present invention, it is very important that the pH of the slurry of the reaction solution remains non-acidic. The pH is 6 or higher, preferably between 7 and 11, more preferably between 7.5 and 10. This is because the composite salt formed is stable in a neutral to alkaline region but it is dissolved or decomposed in at acidic pH. Therefore, when the pH is controlled in the alkaline region within the above-mentioned range, the three starting materials for the salt do not necessarily have to be added simultaneously. It is also possible to add the components stepwise in small portions. However, it is preferable to add the components simultaneously.

During production of the salt, the smaller the pH fluctuation of the slurry, the better the stirring property of the slurry. The fluctuation of the pH is preferably at most 1 pH unit, more preferably at most 0.6 pH unit, and, most preferably, at most 0.1 pH unit.

In the reaction of forming the composite salt in the present invention, it is also preferable to maintain the concentration of dissolved lysine in the slurry between 2 and 40 wt %, i.e., greater than 2% and up to 40% by weight. More preferably, the amount of lysine is 3 wt % to 40 wt %. These weight percents are based on the total weight of the slurry. These ranges in the weight percent of lysine in the slurry include all specific values and subranges therebetween, including 4, 5, 10, 15, 20, 25, 30 and 35% by weight.

A large amount of lysine base in the slurry of is preferably used to keep the pH of the slurry of the reaction solution alkaline. This is because the lysine base has a high water-solubility and the large amount of lysine provides a buffering effect, which reduces the pH fluctuation during the reaction.

In the reaction of forming the composite salt in the present invention, the crystal component obtained depends on the concentration of dissolved lysine and phosphoric acid in slurry solution. That is, when the pH of the slurry of the reaction solution is from 8.5 to 9.5, the concentration of dissolved lysine in reaction slurry solution is at least 17 wt %, more preferably at least 20 wt %, and the concentration of phosphoric acid at least 1 wt %, the aggregate crystals are composed mainly of the first type of crystal component described above. When the pH of the slurry of the reaction solution is set at a slightly lower value of from 7.9 to 8.5, the concentration of dissolved lysine in reaction slurry solution between 2 and 15 wt % and the concentration of phosphoric acid at least 0.2 wt %, the aggregate crystals are composed mainly of the second type of crystal component. A mixture of aggregate crystals composed of the first type and the second type of crystal component are obtained, when concentration of dissolved lysine in reaction slurry solution between 15 and 17 wt %. On the other hand, inorganic crystals free of lysine are obtained when the concentration of dissolved lysine in the reaction slurry is 2 wt % or less.

In this manner, it is possible to add the three starting materials separately for controlling the pH. However, the addition of the alkaline component and the acid component is preferable in view of the control of the reaction. Specifically, there is a method in which lysine that is alkaline and magnesium hydroxide or magnesium oxide have been mixed with each other, followed by adding addition of phosphoric acid. It is also possible to add at same time, lysine that is alkaline and magnesium hydrogen phosphate that is acidic.

With respect to the amounts of the starting materials, the amount of the magnesium component is between 0.95 and 1.43 mols per mol of the phosphoric acid component. It is advisable to use lysine in a large amount. It is usually at least 0.25 mols per mol of the phosphoric acid component.

The temperature is also important in the reaction for forming the composite salt. The temperature is preferably 50° C. or higher, more preferably between 55 and 80° C., inclusive of all specific values and subranges therebetween. When the reaction of forming the composite salt is conducted at temperatures less than 50° C., the slurry of the reaction solution may become too viscous, and the solid-liquid separability of the crystals formed may decrease. When the temperature is higher than 50° C., the composite salt crystals formed exhibit an excellent precipitability and have an excellent solid-liquid separability, and the viscosity of the slurry tends to be stable. As the temperature changes, the pH also changes. Thus, the reaction is preferably conducted by reducing the fluctuation of the temperature as much as possible. It is particularly preferred to conduct the reaction where the fluctuation of the temperature is within the range of ±3° C.

It is preferable to add the starting materials slowly because, when they are added rapidly, the pH cannot be controlled by the increase in the temperature due to generation of reaction heat. When the reaction is continuously conducted using a bath-type flowing reactor, it is preferable to adjust the rate of the addition of the starting materials such that the average residence time of the reaction slurry is 30 minutes or more when the materials are deemed to be completely mixed. The residence time is preferably 1 hour or more. Further, when the reaction is conducted using a batchwise reactor, it is advisable to secure the same residence time. From the quantitative standpoint, since the amount of the slurry is small at the initial stage of the reaction, the starting materials have to be added slowly. However, since the amount of the slurry increases with the addition of the starting materials, the rate of the addition may be increased.

The reaction of forming the composite salt in the present invention is a non-uniform reaction in which the three components, for example, a lysine base in the form of an aqueous solution, phosphoric acid and solid magnesium hydroxide or magnesium oxide, are reacted to form a solid composite salt. Accordingly, these components are preferably fully mixed with one another. Tho mixing in conducted by using a stirring vane, by blowing of air or by circulation of the reaction slurry with a pump or the like.

The slurry containing the composite salt formed by the reaction may be subjected to solid-liquid separation through filtration, centrifugal separation, stationary precipitation or centrifugal precipitation and to washing of a mother liquor, making it possible to isolate the composite salt crystals.

The isolated composite salt may be used directly as a feed additive or may be further processed through granulation. It may also be used as an intermediate for preparing a composite salt composition having an increased stability in a rumen of a ruminant. Examples of such a composite salt composition include a composition obtained by treating the composite salt of the present invention with an aqueous solution of a salt of a polyvalent metal such as calcium, iron, zinc or aluminum, and a composition obtained by treating the composite salt with an aqueous solution of a salt of a polyvalent metal such as calcium, iron, zinc or aluminum in the presence of condensed phosphoric-acid or polyphosphoric acid.

When producing these products, using the composite salt provides excellent slurry properties in these reactions as compared to the composite salt produced by the conventional four processes described above. The reason is that only the surface portion of the starting composite salt participates in the reaction with the salt of the polyvalent metal such as calcium or the like, and a product which retains the spherical shape of the original composite salt is obtained.

Since the composite salt of the present invention is insoluble in neutral or alkaline water and is soluble in an acid, it can be used as a ruminant feed additive composition or a marine animal feed additive composition. That is, the crystals of the composite salt of the present invention are stable in a neutral rumen solution or seawater, and are dissolved in an abomasum of a ruminant or in digestive organs of marine animals by an acidic digestive fluid to elute lysine into the digestive fluid. Since such a property is exhibited in the form of a crystal powder, mixing with another feed composition or mechanical destruction through granulation does not adversely affect the composition. Thus, it can be used as a general-purpose feed additive.

The composite salt of the present invention can be used as a ruminant feed additive composition or a marine animal feed additive composition through granulation. Since the composite salt in insoluble in neutral or alkaline water and is soluble in an acid, the granulation method is not particularly limited. It is possible to employ a general molding method and to use additives such as a binder and the like. Further, the granules may contain other biologically active substances, for example, other essential amino acids other than lysine, vitamins, saccharides and proteins, hormones, insecticides and other animal feed chemicals, so long as the granules are insoluble in neutral or alkaline water and are soluble in acidic aqueous solutions.

EXAMPLES

Having generally described this invention, a further understanding can be obtained by reference to certain specific examples which are provided herein for purposes of illustration only and are not intended to be limiting unless otherwise specified.

The lysine content in the Examples was measured by liquid chromatography. The content of phosphorus and magnesium was measured by ICP (inductively coupled plasma) emission spectrometry. The content of lysine derived from the mother liquor adhered was measured as follows. That is, 50 ml of pure water were added to 100 mg of the sample formed, and the mixture was stirred at room temperature for 30 seconds. The reaction solution was then filtered, and the lysine content of the filtrate was measured. The resulting lysine was defined as lysine derived from the mother liquor adhered. The average filtration specific resistance as an index of slurry properties was measured using a constant-pressure filtration test device (filtration area: 100 cm$^2$, filtration pressure: 400 mmHg).

Example 1

Figure 1A:
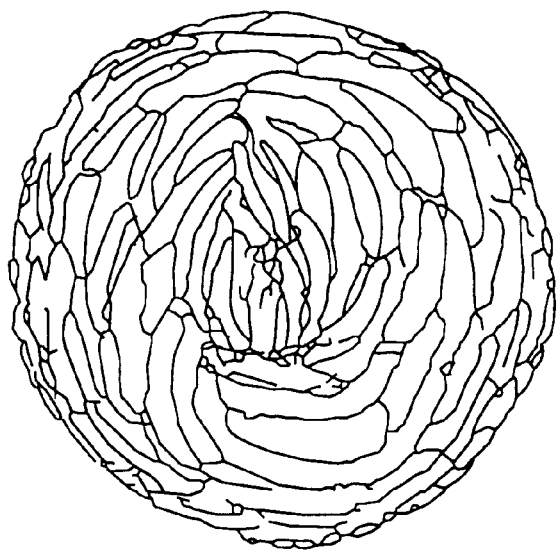
FIGS. 1(a) and 1(b) are views of the novel aggregate crystals of a phosphoric acid/lysine/magnesium composite salt of the present invention; (A) is a complete view, and (B) is a partial view.
Figure 1B:
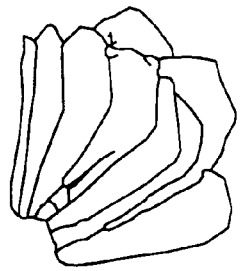

An L-lysine basic aqueous solution (concentration: 50% by weight, 1,550 g) and 860 g of magnesium hydroxide were dispersed into 3,200 ml of water, and the dispersion was mixed with 2,990 g of 37-% phosphoric acid. The mixture was heat-stirred at 80° C. for 3 hours to obtain a viscous first slurry. Twenty liters of water were added to this slurry, and the mixture was stirred in a 120-liter container. To this were added a solution obtained by dispersing 17.9 kg of a 50-% L-lysine basic aqueous solution and 9.84 kg of magnesium hydroxide into 36.8 liters of water and 34 kg of 37-% phosphoric acid over a period of 90 minutes continuously and simultaneously. During that time, the temperature of the reaction solution was maintained at from 69 to 72° C., and the pH was within the range of from 8.2 to 8.5. The fluidity of this second reaction slurry was excellent, and the stirring was conducted without difficulty. The average filtration specific resistance of the slurry was α–1.6×1010 m/kg. This slurry (53 kg) was separated by shaking, and the crystals were washed with 36 liters of water. The amounts of the wet crystals were 27.3 kg. These crystals were dried in an air stream of 80° C. to give 12.4 kg of dry crystals. The dry crystals had a spherical shape. The lysine content of the dry crystals was 20%, and the content of lysine derived from the mother liquor adhered was 3.4% of the dry crystals. The contents of phosphorus and magnesium were 16.7% and 18.9% respectively. FIGS. 1A and 1B are schematic views of the crystals obtained from the electron microphotographs of these crystals.

Comparative Example 1

An L-lysine basic aqueous solution (concentration: 50% by weight, 155 g) and 86 g of magnesium hydroxide were dispersed into 320 ml of water, and the dispersion was mixed with 299 g of 37-% phosphoric acid. The mixture was heat stirred at 80° C. for 3 hours to obtain a viscous first slurry. Two-thousand milliliters of water were added to this slurry, and the mixture was stirred in a 20-liter container. To this were added a solution obtained by dispersing 1,790 g of a 50-% L-lysine basic aqueous solution and 984 g of magnesium hydroxide into 3,680 ml of water and 3,400 g of 37-% phosphoric acid over a period of 90 minutes continuously and simultaneously. During that time, the temperature of the reaction solution was maintained at from 25 to 30° C., and the pH was within the range of from 8.5 to 8.7. The reaction solution became gradually viscous with the addition of the starting solution to produce a second slurry. In order to continue the stirring, 5,000 ml of water were added thereto during the reaction. After the completion of the reaction, the average filtration specific resistance of the second slurry was α=6.8×1011 m/kg. This slurry was separated through shaking, and the crystals were washed with 10,000 ml of water. The amounts of the wet crystals were 7.34 kg. These crystals were dried in an air stream of 80° C. to give 2.98 kg of dry crystals. The lysine content of the dry crystals was 21%, and the content of lysine derived from the mother liquor adhered was 4.6% of the dry crystals. The contents of phosphorus and magnesium were 16.7% and 18.8%, respectively.

Example 2

A portion of the second slurry (19.5 kg) obtained in Example 1 was charged into a 30-liter container, and heat-stirred at 55° C. To this were added a solution obtained by dispersing 50.48 kg of a 50-% lysine basic aqueous solution and 27.72 kg of magnesium hydroxide in 155.5 liters of water and 42.22 kg of 85-% phosphoric acid over a period of 15 hours continuously and simultaneously. During that time, the temperature of the slurry was maintained at 55° C., and the rate at which to add the dispersion of lysine and magnesium hydroxide and phosphoric acid was adjusted such that the pH of the slurry was maintained at 8.3±0.1. The amount of the solution in the container was maintained constant by withdrawing from the container the slurry in the same amount as that of the slurry added. This procedure was conducted for 15 hours, and 265.8 kg of the slurry were withdrawn from the container. The average filtration specific resistance of this slurry was α=2.9×109 m/kg. This slurry (3.46 kg) was separated through shaking, and the crystals were washed with 2.5 liters of water. The resulting wet crystals (1.94 kg) were dried in an air stream of 80° C. to give 0.97 kg of dry crystals. The dry crystals had a spherical shape (see FIG. 8). The lysine content of the dry crystals was 15.3%, and the content of lysine derived from the mother liquor adhered was 0.77% of the dry crystals. Further, the contents of phosphorus and magnesium were 18.1% and 19.1%, respectively.

Comparative Example 2

Figure 2:
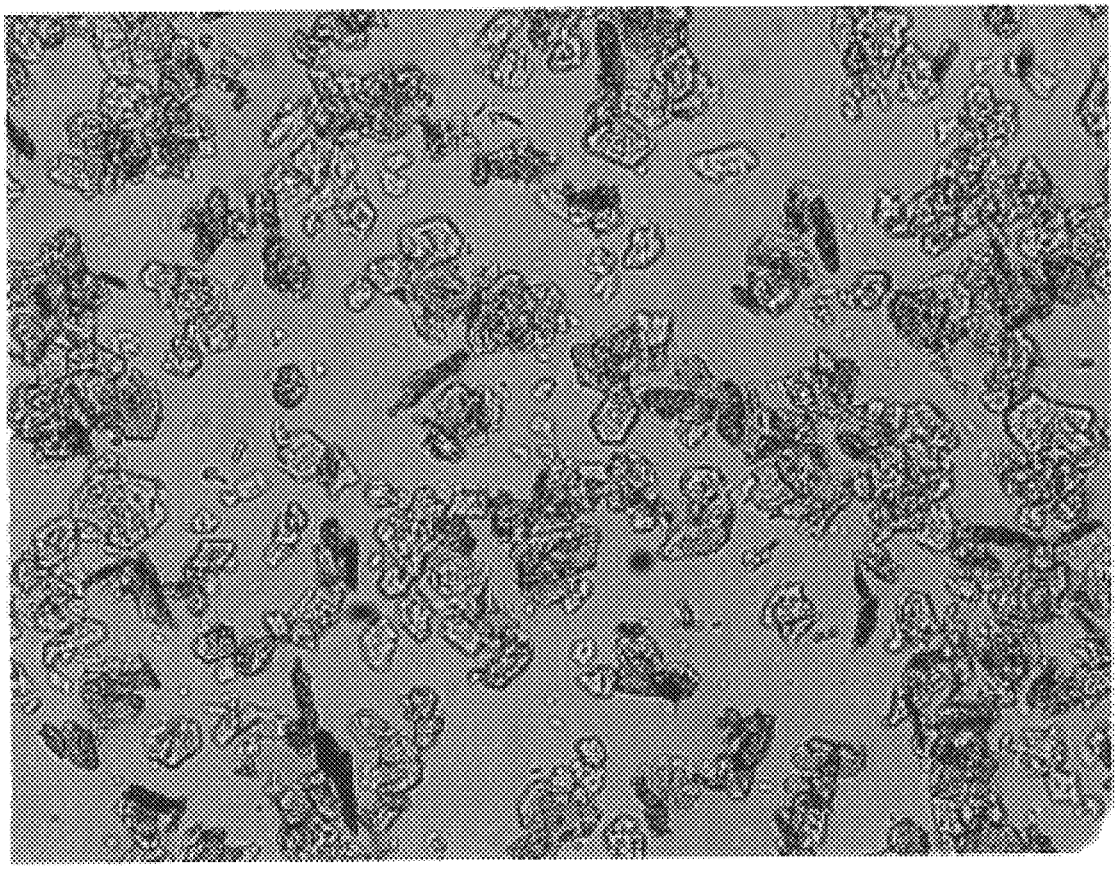
FIG. 2 is an optical electron microphotograph of crystals of a phosphoric acid/lysine/magnesium composite salt obtained in Comparative Example 1.

A solution composed of 650 g of 45% by weight of an L-lysine basic aqueous solution and 461.2 g of 85-% phosphoric acid was mixed with a dispersion of 291.7 g of magnesium hydroxide in 1.0 liter of water. Five minutes later, the reaction was conducted, and the heat generation occurred to produce a white solid. This white solid was heated at 95° C. for 3 hours, and 3.0 liters of water were then added thereto. The mixture was fully milled, and the solid was filtered. The crystals formed were washed with 3.0 liters of water to obtain 2,000 g of wet crystals. The wet crystals were dried at 60° C. under reduced pressure to give 750 g of a white powder. The crystals had an uneven shape. The lysine content of the dry crystals was 19.5%, and the content of lysine derived from the mother liquor adhered was 9.5% of the dry crystals. The contents of phosphorus and magnesium were 16.5% and 16.2%, respectively. FIG. 2 is an optical microphotograph of the dry crystal obtained by this process.

Example 3

The slurry (48 g) obtained in Example 2 was charged into a 300-milliliter flask, and heat-stirred at 60° C. A solution obtained by dispersing 41.5 g of a 50-% lysine basic aqueous solution and 15.8 g of magnesium oxide into 85 ml of water was added thereto in small portions of from 2 to 3 ml every 2 or 3 minutes while maintaining the slurry temperature at 60° C. During that time, the pH was maintained at 8.3 t 0.5 with the addition of 37-% phosphoric acid. This procedure took 2 hours. During that time, the stirring of the reaction slurry was conducted without any difficulty. The resulting slurry was subjected to separation through suction filtration, and the crystals were washed with 490 ml of water. The resulting wet crystals (111 g) were dried overnight at 65° C. under reduced pressure to give 54.1 g of dry crystals. The crystals had a spherical shape. The lysine content of the dry crystals was 15.4%, and the content of lysine derived from the mother liquor adhered was 1% of the dry crystals.

Example 4

Magnesium secondary phosphate 3-hydrate (174.3 g) was added to 3,000 g of an L-lysine basic aqueous solution (concentration: 25% by weight), and the mixture was heat-stirred at 80° C. for 3 hours. Subsequently, particulate crystals of magnesium secondary phosphate 3-hydrate disappeared, and fine crystals were formed in large amounts. The resulting reaction solution was maintained at 60° C., 1,300 g of an L-lysine basic aqueous solution (concentration: 45% by weight) and 522.9 g of magnesium secondary phosphate 3-hydrate were added thereto in small portions over a period of 15 hours, and the mixture was stirred. During this time, the pH of the reaction solution was constant at 9.5. After the completion of the reaction, the stirring was continued for 30 minutes. When the reaction solution stood still, large amounts of white crystals were precipitated on the bottom of the container. The stirring was conducted again, and the average filtration specific resistance of the resulting slurry was measured, $\alpha=3.4\times10^9$ m/kg. This slurry was separated through shaking, and the crystals were washed with 3.5 liters of water. The resulting wet crystals (1.98 kg) were dried in an air stream of 80° C. to give 1.14 kg of dry crystals. The dry crystals had a spherical shape. The lysine content of the dry crystals was 51.1%. The contents of phosphorus and magnesium were 10.0% and 8.5%, respectively.

Example 5

One hundred grams of the dry crystals obtained in Example 4 were added to 3,000 g of an L-lysine basic aqueous solution (concentration: 25% by weight), and the temperature of the solution was maintained at 60° C. While 1,200 g of an L-lysine basic aqueous solution (concentration: 45% by weight) were intermittently added in portions of 200 g every 2 hours, a solution of 461 g of 85-% phosphoric acid in 500 g of water was continuously added at a rate of 96.1 g/hr and a slurry obtained by dispersing 233.4 9 of magnesium hydroxide into 1,000 ml of water was added at a rate of 123.3 g/hr, and the mixture was stirred. During this time, the pH of the reaction solution was constant at 9.5. After the completion of the addition, the average filtration specific resistance of the resulting slurry was measured, and it was found to be $\alpha=2.4\times10^9$ m/kg. This slurry was separated through shaking, and the crystals were washed with 3.4 liters of water. The resulting wet crystals (1.99 kg) were dried in an air stream of 80° C. to give 1.24 kg of dry crystals. The dry crystals had a spherical shape (see FIG. 6). The lysine content of the dry crystals was 51.1%, and the contents of phosphorus and magnesium were 10.8% and 8.5% respectively. The dry crystals were smelled, and found to be almost odorless.

Comparative Example 3

One thousand grams of an L-lysine basic aqueous solution (concentration: 45% by weight) and 230.6 g of 85-% phosphoric acid were dissolved in 1,200 ml of water, and a slurry obtained by dispersing 116.7 g of magnesium hydroxide into 500 ml of water was added thereto. The solution was stirred. The resulting mixture gradually became a viscous slurry. When the slurry was continuously diluted with water to continue the stirring, the addition of 1,000 ml of water was required. During this time, the slurry temperature was maintained at 30° C. or lower. The average filtration specific resistance of the resulting slurry was $\alpha=9.2\times10^{11}$ m/kg. The resulting slurry was filtered under reduced pressure, and washed with 3,500 ml of water to obtain 1,500 g of wet crystals. The wet crystals were dried at 60° C. under reduced pressure to give 570 g of dry crystals. The dry crystals were fine crystals. The lysine content was 47.6%, and the contents of phosphorus and magnesium were 10.8% and 8.5% respectively. The dry crystals were smelled, and found to have the strong amino odor peculiar to the lysine base.

Example 6

Figure 3:
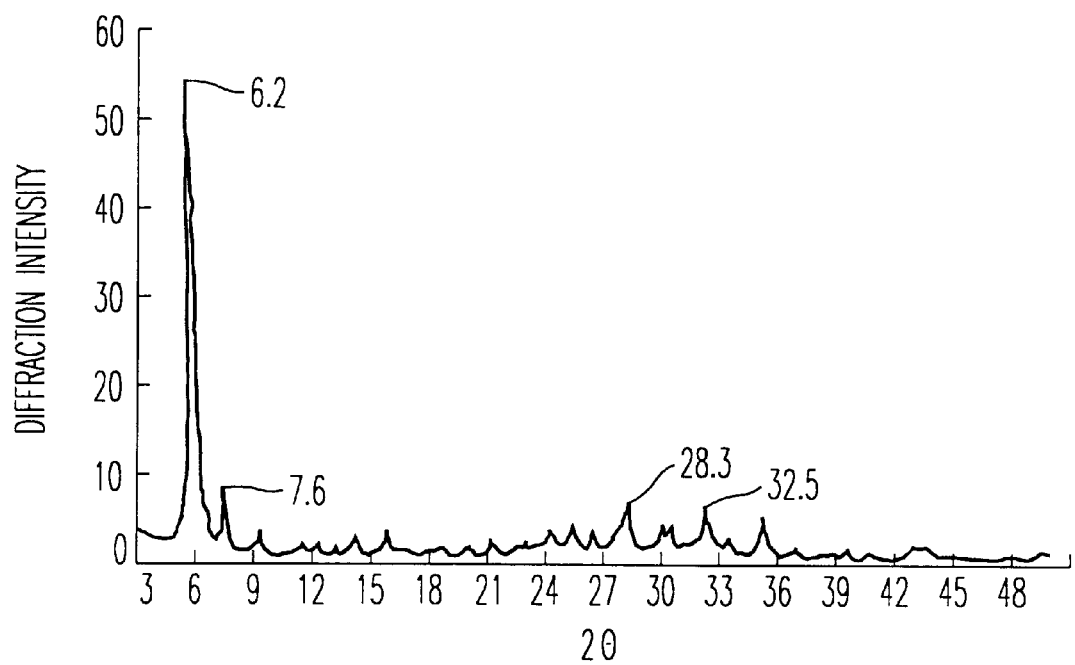
FIG. 3 is a powder X-ray diffraction pattern of the novel aggregate crystals of a phosphoric acid/lysine/magnesium composite salt of the present invention obtained in Example 2.
Figure 4:
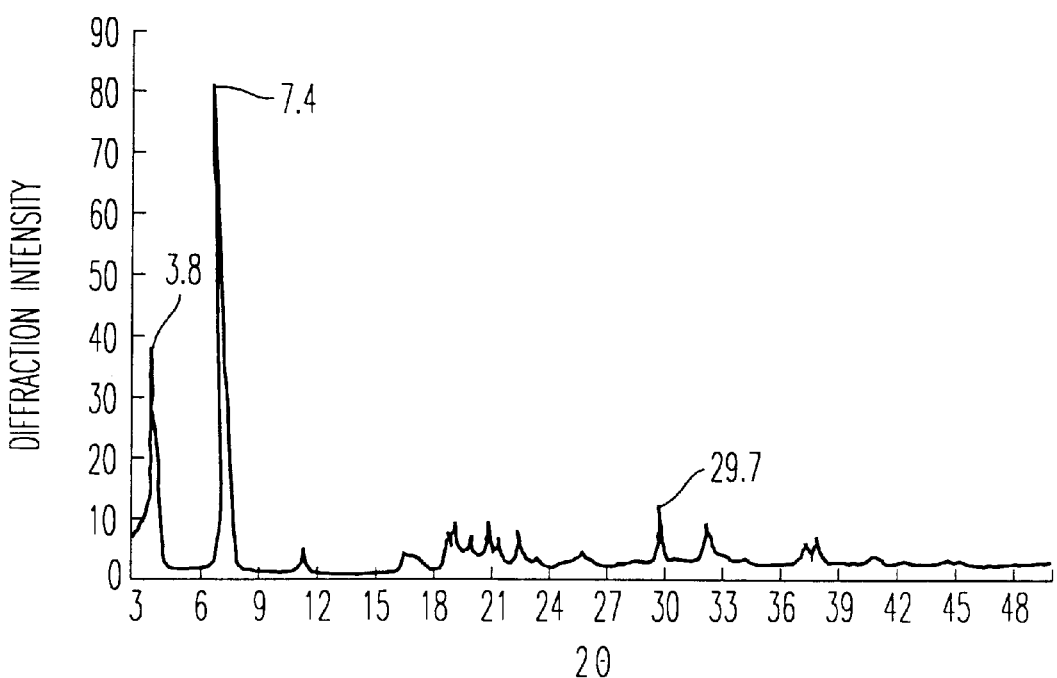
FIG. 4 is a powder X-ray diffraction pattern of the novel aggregate crystals of a phosphoric acid/lysine/magnesium composite salt of the present invention obtained in Example 5 of the present disclosure.

With respect to the dry crystals obtained in Examples 2 and 5, powder X-ray diffraction spectra were measured using copper Ka rays. The resulting spectra ave shown in FIGS. 3 and 4.

Example 7

The wet crystals (26.95 kg) of the composite salt obtained In Example 1 were added to 46.5 liters of water, and the mixture was stirred at 40° C. (slurry concentration: 16.7%). To this were added 1.4 kg of calcium hydroxide, and the mixture was stirred for 2 hours. During this procedure, solidification and gelation of the slurry did not occur, and the stirring was conducted without trouble. The average filtration specific resistance of the slurry was $\alpha=7.6\times10^{10}$ M/kg.

The thus-obtained slurry was separated through shaking, and the crystals were washed with 63 liters of water. The wet crystals (28.7 kg) obtained were dried in an air stream of 80° C. to give 9.64 kg of dry crystals. The crystals, like the starting composite salt, had a spherical shape. The lysine content was 12.6%, and the content of lysine derived from the mother liquor adhered was less than 0.06% (less than the limit of the lysine content detected) of the dry crystals.

Comparative Example 4

Ninety grams of the dry crystals obtained in Comparative Example 1 were added to 450 ml of water, and the mixture was stirred at 40° C. (slurry concentration; 16.7%). However, since the stirring was difficult owing to the poor slurry properties, 200 ml of water were added thereto (slurry concentration: 12.2%). Ten grams of calcium hydroxide were added thereto, and the mixture was stirred for 2 hours. However, the slurry properties were gradually worsened. The resulting slurry was separated through auction filtration, and the crystals were washed with 450 ml of water. The wet crystals (285 g) obtained were dried overnight at 65° C. under reduced pressure to give 86.4 g of dry crystals. The crystals had the same uneven shape as the starting magnesium salt. The lysine content was 8.3%, and the content of lysine derived from the mother liquor adhered was 0.3% of the dry crystals.

Example 8

The slurry (22.15 kg) of the composite salt obtained in Example 2 was stirred at 55° C. To this were added an aqueous solution of 0.9 kg of pyrophosphoric acid in 8.4 liters of water and a slurry obtained by dispersing 1.22 kg of calcium hydroxide into 8.1 liters of water simultaneously over a period of 2 hours. During that time, the pH of the reaction slurry was maintained at 9.3. During the reaction, solidification and gelation of the slurry did not occur, and the stirring was conducted without difficulty. The resulting slurry was separated through shaking, and washed with 40 liters of water. The average filtration specific resistance of this slurry was $\alpha=1.8\times1010$ m/kg. The wet crystals were dried in an air stream of 90° C. to give 6.86 kg of dry crystals. The crystals had the same spherical shape as the starting composite salt. The lysine content was 11.0%, and the content of lysine derived from the mother liquor adhered was 0.2% of the dry crystals.

Example 9

With respect to the composite salts obtained in Examples 1 to 5, 7 and 8, the solubility thereof in a lumen solution, seawater or an abomasum solution was measured, and the results are shown in Table 1. Regarding the rumen solution, the following McDougall buffer solution was used as a model rumen solution. A commercial ready-made salt composition (artificial seawater) for seawater fish which had been dissolved at a predetermined concentration was used as seawater. Regarding the abomasum solution, the following acetate-phosphate buffer solution was used as a model abomasum solution. Two-hundred milliliters of each of the test solutions were charged into a 300-milliliter conical flask. Then, 500 mg of each of the samples were charged therein. The model rumen solution was shaken at 39° C. for 24 hours, the artificial seawater at 25° C. for 2 hours and the model abomasum solution at 39° C. for 1 hour respectively. After the completion of the shaking, the amount of lysine eluted was measured, and the protection and the elution in each of the solutions was calculated. The protection was expressed in terms of a value obtained by subtracting the value of elution from 1.

*McDougall buffer solution:
Buffer solution obtained by dissolving the following reagents into 1,000 ml of water.

| | |
|---|---|
| sodium hydrogencarbonate | 7.43 g |
| disodium hydrogen phosphate 12-hydrate | 7.00 g |
| sodium chloride | 0.34 g |
| potassium chloride | 0.43 g |
| magnesium chloride 6-hydrate | 0.10 g |
| calcium chloride | 0.05 g |

*Acetate-phosphate buffer solution
Buffer solution prepared by dissolving the following reagents into 1,000 ml of water and adjusting the pH of the solution to 2.2 with hydrochloric acid.

| | |
|---|---|
| sodium dihydrogenphosphate 2-hydrate | 1.95 g |
| sodium acetate 3-hydrate | 3.40 g |

TABLE 1

Protection and elution of a composite salt unit: (%)

| | Lysine content | Content of lysine derived from mother liquor adhered | Protection in lumen solution | Protection in seawater | Elution in abomasum solution |
|---|---|---|---|---|---|
| Example 1 | 20.0 | 3.4 | 29.1 | 45.7 | 100.0 |
| Example 2 | 15.3 | 0.77 | 36.4 | 52.9 | 100.0 |
| Example 3 | 15.4 | 1.0 | 35.9 | 52.3 | 100.0 |
| Example 4 | 51.1 | 2.6 | 9.5 | 15.0 | 100.0 |
| Example 5 | 49.1 | 0.6 | 9.7 | 15.6 | 100.0 |
| Example 7 | 12.6 | <0.06 | 92.4 | 95.3 | 100.0 |
| Example 8 | 11.0 | 0.2 | 95.1 | 96.4 | 100.0 |

Example 10

Three-hundred grams of the dry crystals obtained in Example 2, 20 g of a methionine powder, 50 g of calcium carbonate, 30 g of casein sodium and 59 of starch sodium glycolate were mixed, and kneaded with the addition of 100 ml of water. The mixture was then extruded using a disc pelleter having a bore diameter of 2 mm. The resulting product was cut to a length of approximately 2 mm, dried, and molded into a granule having a diameter of approximately 2 mm. The thus-obtained granule was cut into small pieces having a diameter of approximately 0.5 mm. The five small pieces were heat-extracted with dilute hydrochloric acid, and the amino acid content was measured. Consequently, no difference in the amino acid content was found among these small pieces. With respect to the resulting granule, the protection in the corresponding lumen solution and the elution in the corresponding abomasum solution were evaluated. As a result, the protection in the corresponding lumen solution was 97% in lysine and 64% in methionine. The elution in the corresponding abomasum solution was 95% in both lysine and methionine. Further, with respect to the small pieces having the diameter of approximately 0.5 mm, the protection in the corresponding rumen solution and the elution in the corresponding abomasum solution were likewise measured. As a result, the protection in the corresponding lumen solution was 95% in lysine and 62% in methionine. The solution in the corresponding abomasum solution was 98% in both lysine and methionine.

Obviously, additional modifications and variations of the present invention are possible in light of the above teachings. It is therefore to be understood that within the scope of the appended claims, the invention may be practiced otherwise than as specifically described herein.

This application is based on Japanese Application No. 226532/1996 filed on Aug. 28, 1996 and incorporated herein by reference in its entirety.

What is claimed as new and desired to be secured by Letters Patent of the United States is:

1. A spherical aggregate crystal comprising a phosphoric acid/lysine/magnesium composite salt represented by formula (1):

$$R_a Mg_b H_c PO_4 \cdot (H_2O)_n \qquad (1)$$

wherein

R is a lysine cation;

a is 0.15 to 1.0;

b is 1.0 to 1.42;

c is 0 to 0.3;

n is 0 to 10; and a+(2×b)+c=3.

2. The spherical aggregate crystal of claim 1, wherein the crystal has a long axis/short axis ratio of 1 to 2.

3. The spherical aggregate crystal of claim 1, wherein a is 1, b is 1, c is 0, and n is 2.

4. The spherical aggregate crystal of claim 3, wherein the powder X-ray diffraction spectrum of the composite salt has main peaks angles (0) of about 3.7°, about 7.4°, about 18.5°, about 18.8°, about 20.7°, about 22.2°, about 29.7° and about 32.3°, using copper Kα rays.

5. The spherical aggregate crystal of claim 3, wherein the crystal has a long axis/short axis ratio of 1 to 2.

6. The spherical aggregate crystal of claim 1, wherein a is 0.21 to 0.25;

b is 1.325 to 1.395;

c is 0 to 0.1; and n is 0 to 5.

7. The spherical aggregate crystal of claim 6, wherein the powder X-ray diffraction spectrum of the composite salt has main peaks at angles (0) of from about 6.0° to about 6.5°, from about 7.4° to about 7.7°, about 15.6°, about 28.2° and about 32.5°, using copper Kα rays.

8. The spherical aggregate crystal of claim 6, wherein the crystal has a long axis/short axis ratio of 1 to 2.

9. A composition comprising a plurality of the spherical aggregate crystal of claim 1, wherein each crystal has substantially the same diameter.

10. A animal feed additive composition containing granules which comprise the spherical aggregate crystal of claim 1.

11. The animal feed additive composition of claim 10, wherein the granules further comprise at least one member selected from the group consisting of amino acids other than lysine, vitamins, saccharides, proteins, hormones and insecticides, wherein the granules are insoluble in neutral or alkaline aqueous solutions, but are soluble in acidic aqueous solutions.

12. A process for producing spherical aggregate crystals comprising a phosphoric acid/lysine/magnesium composite salt represented by formula (1):

$$R_a Mg_b H_c PO_4 \cdot (H_2O)_n \qquad (1)$$

wherein

R is a lysine cation;

a is 0.15 to 1.0;

b is 1.0 to 1.42;

c is 0 to 0.3;

n is 0 to 10; and a+(2×b)+c=3, comprising adding lysine, a magnesium component and a phosphoric acid component to a slurry containing crystals of the composite salt represented by formula (1), followed by mixing.

13. The process of claim 12, wherein the lysine, the magnesium component and the phosphoric acid component are added simultaneously to the slurry.

14. The process of claim 12, wherein the pH of the slurry is maintained at least 6, and the temperature is maintained at least 50° C.

15. The process of claim 12, wherein the pH of the slurry is maintained from 7 to 11, and the pH fluctuates at most 1 pH unit when the lysine, the magnesium component and the phosphoric acid component are added to the slurry and mixed therein.

16. The process of claim 12, wherein the pH of the slurry is maintained from 8.5 to 9.5; the slurry comprises, in total, at least 17% by weight of the lysine; a is 1; b is 1; c is 0; and n is 2.

17. The process of claim 12, wherein the pH of the slurry is maintained from 7.8 to 8.8; the slurry comprises, in total, 2 to 15% by weight of the lysine; a is 0.21 to 0.25; b is 1.325 to 1.395;c is 0 to 0.1; and n is 0 to 5.

18. The process of claim 12, wherein the magnesium component comprises a magnesium salt and the phosphoric acid component comprises phosphoric acid or a phosphoric acid salt, or both.

19. The spherical aggregate crystals produced by the process of claim 12.

20. A method of supplementing the diet of an animal with lysine comprising feeding the spherical aggregate crystal of claim 1 to the animal.

* * * * *